US 9,931,448 B2

United States Patent
Pratt et al.

(10) Patent No.: US 9,931,448 B2
(45) Date of Patent: Apr. 3, 2018

(54) SYSTEM AND METHOD FOR MULTIPLE DIRECTION FLEXIBLE INLINE CANISTER

(71) Applicant: KCI Licensing, Inc., San Antonio, TX (US)

(72) Inventors: Benjamin Andrew Pratt, Poole (GB); Colin John Hall, Poole (GB); Christopher Brian Locke, Bournemouth (GB); Elliott James Rider, Acklam (GB); Gareth Stephenson, Southampton (GB)

(73) Assignee: KCI Licensing, Inc., San Antonio, TX (US)

( * ) Notice: Subject to any disclaimer, the term of this patent is extended or adjusted under 35 U.S.C. 154(b) by 899 days.

(21) Appl. No.: 14/204,671

(22) Filed: Mar. 11, 2014

(65) Prior Publication Data
US 2014/0276492 A1    Sep. 18, 2014

Related U.S. Application Data

(60) Provisional application No. 61/802,888, filed on Mar. 18, 2013.

(51) Int. Cl.
*A61M 1/00* (2006.01)
*A61M 5/178* (2006.01)
(Continued)

(52) U.S. Cl.
CPC ........ *A61M 1/0094* (2014.02); *A61M 1/0001* (2013.01); *A61M 1/0015* (2014.02);
(Continued)

(58) Field of Classification Search
CPC .......... A61M 1/00; A61M 5/178; A61M 5/00; A61M 5/32; A61M 35/00; A61F 13/00
See application file for complete search history.

(56) References Cited

U.S. PATENT DOCUMENTS 1,355,846 A    10/1920    Rannells
2,547,758 A     4/1951    Keeling
(Continued)

FOREIGN PATENT DOCUMENTS

AU    550575 A1    3/1986
AU    745271       4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).
(Continued)

*Primary Examiner* — Michele Kidwell
*Assistant Examiner* — Ilya Treyger

(57) ABSTRACT

A system and apparatus for treating a tissue site with reduced pressure and collecting fluids from the tissue site is disclosed. The system may include a reduced-pressure source, a pouch in fluid communication with the reduced pressure source, and a dressing in fluid communication with the pouch. The pouch may include a first wall, a second wall having a periphery coupled to the first wall to form an interior, and a third wall extending through the interior to form a first chamber in fluid communication with the dressing and a second chamber in fluid communication with the reduced pressure source. A plurality of filters are positioned in the third wall. The filters permit fluid communication between the first chamber and the second chamber.

26 Claims, 11 Drawing Sheets

(51) Int. Cl.
*A61M 5/00* (2006.01)
*A61M 5/32* (2006.01)
*A61M 35/00* (2006.01)

(52) U.S. Cl.
CPC ........ *A61M 1/0052* (2014.02); *A61M 1/0088* (2013.01); *A61M 1/0096* (2014.02); *A61M 2205/21* (2013.01); *A61M 2205/7536* (2013.01); *Y10T 29/49826* (2015.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0137539 A1 | 6/2005 | Biggie et al. |
| 2005/0186183 A1 | 8/2005 | DeAngelo et al. |
| 2006/0079852 A1 | 4/2006 | Bubb et al. |
| 2010/0108596 A1 | 5/2010 | Duhaut et al. |
| 2011/0152799 A1 | 6/2011 | Kevin et al. |
| 2013/0053797 A1 | 2/2013 | Locke et al. |
| 2013/0304004 A1 | 11/2013 | Riesinger |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/010424 | 9/1990 |
| WO | 93/09727 | 5/1993 |
| WO | 94/020041 | 9/1994 |

(56) References Cited

FOREIGN PATENT DOCUMENTS

| WO | 96/05873 | 2/1996 |
|---|---|---|
| WO | 97/18007 | 5/1997 |
| WO | 99/13793 | 3/1999 |
| WO | 2009126102 A1 | 10/2009 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đukić, Ž. Maksimović, Đ.. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
Partial International Search Report for corresponding PCT/US2014/023549, dated Aug. 18, 2014.
Extended European Search Report for corresponding application 17163977.6, dated Sep. 15, 2017.

SYSTEM AND METHOD FOR MULTIPLE DIRECTION FLEXIBLE INLINE CANISTER

Under 35 U.S.C. § 119(e), this application claims priority to and the benefit of U.S. Provisional Patent Application No. 61/802,888 filed Mar. 18, 2013, entitled "System and Method for Multiple Direction Flexible Inline Canister," the disclosure of which is hereby incorporated by reference in its entirety.

TECHNICAL FIELD

The present disclosure relates generally to medical treatment systems for treating tissue sites and processing fluids. More particularly, but not by way of limitation, the present disclosure relates to inline storage pouches, systems, and methods for receiving and storing exudates from a tissue site.

BACKGROUND

Caring for wounds is important in the healing process. Wounds often produce considerable exudate. Medical dressings are often used in wound care to address the production of liquids from the wound. If not properly addressed, liquids at the wound can lead to infection or maceration at or near the wound. Wound dressings may be used alone or as an aspect of applying reduced pressure to a tissue site.

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the cost and complexity of negative-pressure therapy can be a limiting factor in its application, and the development and operation of negative-pressure systems, components, and processes continues to present significant challenges to manufacturers, healthcare providers, and patients.

SUMMARY

According to some illustrative embodiments, a system for treating a tissue site with reduced pressure is described. The system may include a reduced-pressure source, a pouch in fluid communication with the reduced pressure source, and a dressing in fluid communication with the pouch. The pouch may include a first wall, a second wall having a periphery coupled to the first wall to form an interior, and a third wall extending through the interior to form a first chamber in fluid communication with the dressing and a second chamber in fluid communication with the reduced pressure source. A plurality of filters may be positioned in the third wall. The filters may permit fluid communication between the first chamber and the second chamber.

According to other illustrative embodiments, a pouch for use with fluids from a tissue site is described. The pouch may include a first wall and a second wall having a peripheral portion coupled to the first wall to form an interior. A third wall may extend through the interior to form a first chamber adapted to be in fluid communication with a dressing and a second chamber adapted to be in fluid communication with a reduced pressure source. A plurality of filters may be positioned in the third wall. The filters may permit fluid communication between the first chamber and the second chamber. Reduced pressure supplied to the second chamber may be supplied to the first chamber through the filters.

According to other illustrative embodiments, a method of manufacturing an inline storage pouch is described. A pouch may be formed having a first chamber and a second chamber, and an absorbent material may be disposed within the first chamber. A manifold may be disposed within the second chamber. A first port may be coupled to the pouch. The first port may be configured to fluidly couple the first chamber to a dressing for receiving fluids. A second port may also be coupled to the pouch. The second port may be configured to fluidly couple the second chamber to a therapy unit for supplying reduced pressure. A plurality of air bridges may be coupled between the first chamber and the second chamber to provide fluid communication between the first chamber and the second chamber.

According to other illustrative embodiments, a method for treating a tissue site with reduced pressure is described. A reduced-pressure source and a dressing proximate to the tissue site to receive liquids from the tissue site may be provided. A pouch may also be provided. The pouch may include a first wall, a second wall coupled to the first wall on peripheral portions of the first wall and the second wall to form an interior, and a third wall extending through the interior to form a first chamber adapted to be in fluid communication with the dressing and a second chamber adapted to be in fluid communication with the reduced pressure source. The pouch may further include a plurality of filter assemblies positioned in the third wall. The filter assemblies may permit fluid communication between the first chamber and the second chamber. Each filter assembly may be separated from adjacent filter assemblies. Reduced pressure supplied to the second chamber may be supplied to the first chamber through the filter assemblies. The reduced-pressure source may be fluidly coupled to the second chamber, and the dressing may be fluidly coupled to the first chamber. Reduced pressure may be supplied to the dressing through the second chamber, filter assemblies, and the first chamber. Liquids may be received and stored in the first chamber in response to the supply of reduced pressure.

According to other illustrative embodiments, an apparatus for storing fluid is described. The apparatus may include a first chamber and a second chamber. The apparatus may further include a first manifold disposed in the first chamber, and a second manifold disposed in the second chamber. At least two air bridges may couple the first manifold and the second manifold. An absorbent may be disposed in the second chamber proximate to the second manifold.

Other aspects, features, and advantages of the illustrative embodiments will become apparent with reference to the drawings and detailed description that follow.

DETAILED DESCRIPTION OF ILLUSTRATIVE EMBODIMENTS

New and useful systems, methods, and apparatuses for providing an inline storage pouch to receive and store exudates from a tissue site, the inline storage pouch to be used with a reduced-pressure system, are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

The example embodiments may also be described herein in the context of reduced-pressure therapy applications, but many of the features and advantages are readily applicable to other environments and industries. Spatial relationships between various elements or to the spatial orientation of various elements may be described as depicted in the attached drawings. In general, such relationships or orientations assume a frame of reference consistent with or relative to a patient in a position to receive reduced-pressure therapy. However, as should be recognized by those skilled in the art, this frame of reference is merely a descriptive expedient rather than a strict prescription.

Figure 1:
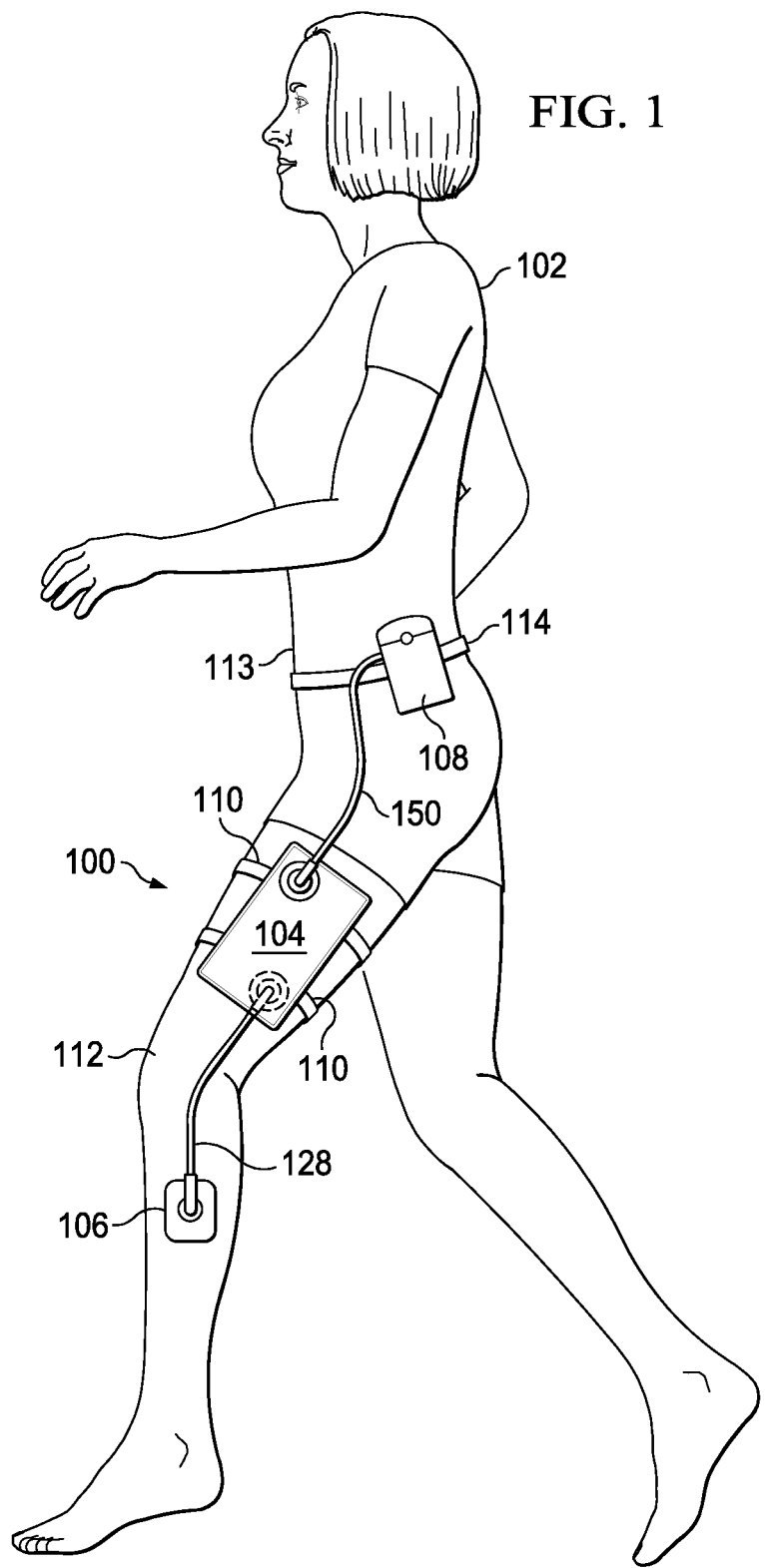
FIG. 1 is a schematic diagram of a reduced-pressure system for treating a tissue site in accordance with some embodiments.

FIG. 1 is a schematic view, illustrating details of an illustrative embodiment of a system 100 for treating a tissue site with reduced pressure. System 100 is shown applied to a human, but system 100 may be used on other types of subjects. System 100 may include an inline storage pouch, such as pouch 104, a reduced-pressure dressing, such as a dressing 106 (or other fluid reception device), and a therapy unit, such as therapy unit 108. In some embodiments, dressing 106 may be fluidly coupled to pouch 104 with a first conduit 128, and pouch 104 may be fluidly coupled to therapy unit 108 with a second conduit 150. Therapy unit 108 may provide reduced pressure, as described in more detail below, through second conduit 150, pouch 104, and first conduit 128 to dressing 106 to remove fluids from a tissue site. Fluids may be delivered to pouch 104 for storage and later removal. In other embodiments, the fluids may be from an ostomy bag or another source rather than dressing 106.

Pouch 104 may include one or more straps 110 configured to mount pouch 104 to person 102. Similarly, therapy unit 108 may also include one or more straps 114, allowing therapy unit 108 to be mounted to person 102. Straps 110 and straps 114 may be elastomeric members, belt-like members, or the like. In addition, straps 110 and straps 114 may be adjustable, permanently secured, or releasably coupled to pouch 104 and therapy unit 108, respectively. In some embodiments, straps 110 and straps 114 may allow positioning of pouch 104 and therapy unit 108 at different locations on person 102 so that the weight of system 100 may be distributed at more than one location of person 102. For example, pouch 104 may be strapped to a portion of person 102, such as a leg 112, using straps 110 or other attachment devices. Similarly, therapy unit 108 may be mounted to another portion of person 102, such as a waist 113, using straps 114. Therapy unit 108 and pouch 104 may also be mounted at locations other than person 102, for example, on a bed, pole, or the like.

Pouch 104 may be flexible, allowing pouch 104 to conform to a portion of the body of person 102, thereby enhancing safety and comfort of person 102. In addition, the flexible nature of pouch 104 may allow pouch 104 to be stored in a small space. Pouch 104 may be relatively easy to manufacture compared to rigid canisters that have been used to collect liquids. Moreover, if pouch 104 is used with animals, the flexible nature may help prevent injury, for example, if the animal bumps surfaces or rolls over. In addition, pouch 104 may be oriented as shown in FIG. 1, or pouch 104 may be oriented in other positions to improve fit to, and comfort of, person 102.

The ability of a flexible canister, such as pouch 104, to work efficiently can be dependent on its orientation during use. Flexible canisters often include filters or filter assemblies to prevent fluids collected from a tissue site from reaching and potentially damaging a reduced-pressure source. As the flexible canister fills with exudates and other fluids from the tissue site, the position of the filter in relationship to the fluid path may affect the performance of the flexible canister. For example, a vertically oriented flexible canister may have a port fluidly connected to the tissue site on an upper end of the flexible canister and a port fluidly connected to a reduced pressure source, such as a device connector, on a lower end of the flexible canister. Fluid may move down the flexible canister from the port fluidly connected to the tissue site to the device connector due to the force of the negative pressure and gravity. Once the fluid reaches the lower end of the flexible canister it may be pulled across the device connector by the negative pressure. The canister may fill from the bottom upwards, and if the filter is positioned proximate to and in the fluid path of the device connector, the filter may become blocked prior to the flexible canister being filled. Blockage of the filter may cause a pressure drop that triggers an alarm and causes the therapy to stop.

In addition, an absorbent may be disposed in the flexible canister to store the fluids from the tissue site. The lower parts of the absorbent proximate to the lower end of the flexible canister may be at full capacity, for example, completely saturated, if the pressure drop occurs. This may be the result of a pooling effect caused by the absorbent being unable to retain any more liquid, allowing the liquid to pool proximate to the device connector and block the filter. A large percentage of the absorbent may not be in proximity to the device connector and may not have been contacted by the liquid, consequently, the absorbent may not fully absorb liquid, leaving a portion of the flexible canister unfilled.

As disclosed herein, system 100 can overcome these shortcomings by providing a flexible canister that manifolds fluid and air to provide a low pressure drop and an increased spread of exudates and other fluids from the tissue site throughout the flexible canister, such as pouch 104. In one particular embodiment, system 100 may provide a multi-directional canister which can be used in a range of different form factors or orientations as a multi-point pressure manifold solution. Multiple orientation use of the flexible canister may permit use of the canister in a wider variety of locations, and persons. In addition, multiple orientation use of the flexible canister may permit the flexible canister to be used in a mobile environment. In other embodiments, system 100 may provide a multi-point pressure manifold solution, such as the pouch 104, having two chambers with a plurality of fluid transfer points, such as filter assemblies, that permit fluid communication between the two chambers. One of the two chambers can store fluids and exudates from the tissue site, and another of the two chambers can bridge a port fluidly coupled to a reduced-pressure source to the chamber, storing fluids at each fluid transfer point within the flexible canister.

Figure 2:
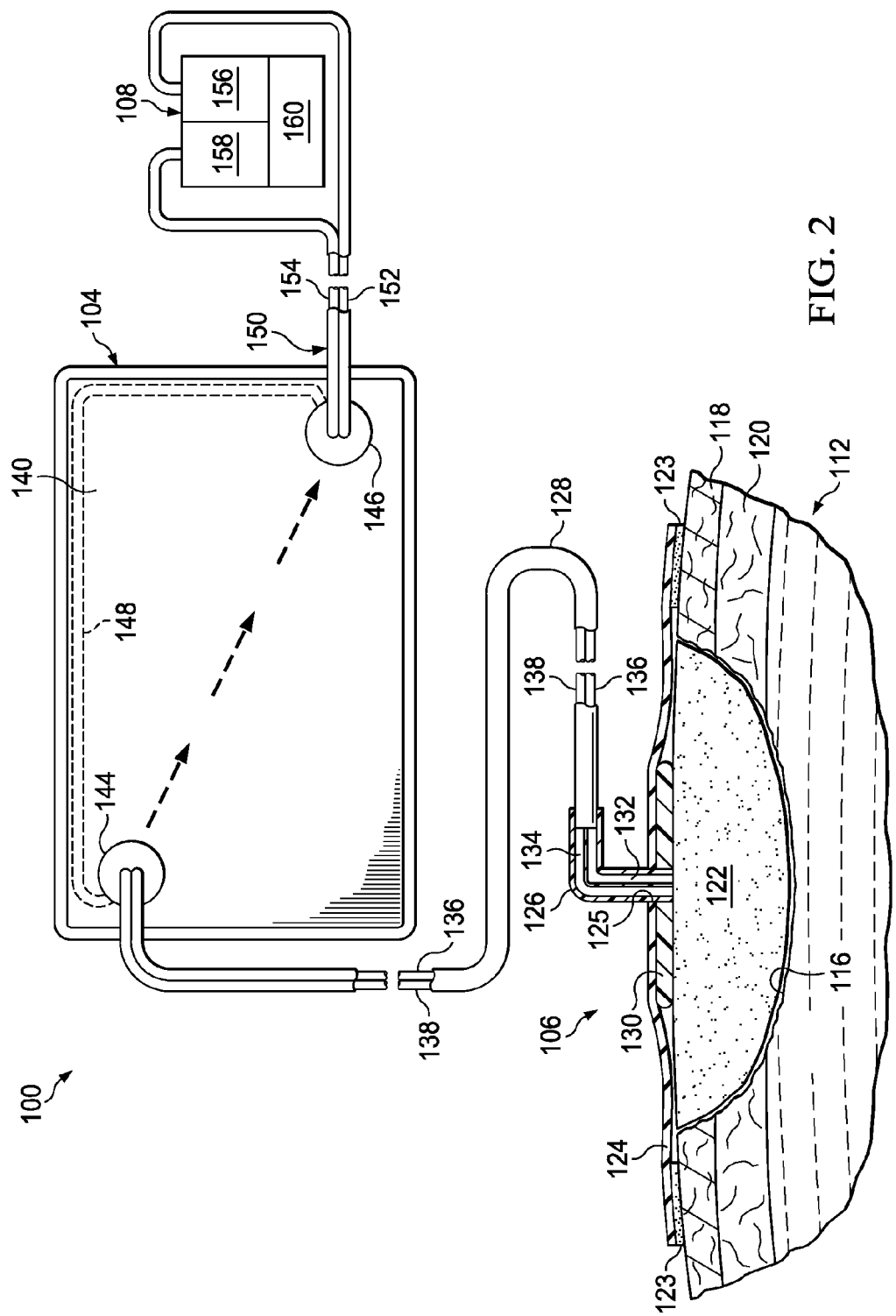
FIG. 2 is a schematic diagram, with a portion shown in cross section and a portion in plan view, of the reduced-pressure system of FIG. 1.

FIG. 2 is a schematic diagram, illustrating additional details that may be associated with some embodiments of system 100, with a portion shown in cross section and a portion in plan view. Dressing 106 may be positioned at a tissue site 116 on leg 112 that extends through epidermis 118 and into dermis 120. The term "tissue site" in this context broadly refers to a wound or defect located on or within tissue of a human, animal, or other organism, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, grafts, and fistulas, for example. The term "tissue site" may also refer to areas of tissue that are not necessarily wounded or defective, but are instead areas in which it may be desired to add or promote the growth of additional tissue. For example, reduced pressure may be used in certain tissue areas to grow additional tissue that may be harvested and transplanted to another tissue location. The term "tissue site" may also include incisions, such as a surgical incision. Tissue site 116 may include epidermis 118, subcutaneous tissue, or other muscle tissue. Tissue site 116 may be surrounded by healthy or undamaged tissue, for example a portion of epidermis 118 that may be undamaged. Treatment of the tissue site 116 may include removal of fluids, for example, exudates or ascites.

In some embodiments, dressing 106 may include a tissue interface, such as manifold 122, a tissue site covering, such as a drape 124, and a connector 126. Manifold 122 may be positioned adjacent to, and in contact with, tissue site 116. Manifold 122 may be positioned proximate to tissue site 116 such that manifold 122 has a first surface that faces tissue site 116 and a second surface that may be opposite the first surface. The term "manifold" as used herein generally refers to a substance or structure that may be provided to assist in applying reduced pressure to, delivering fluids to, or removing fluids from tissue site 116. Manifold 122 may include a plurality of flow channels or pathways that can distribute or collect fluids from across the tissue site 116 around manifold 122. In one illustrative embodiment, the flow channels or pathways may be interconnected to improve distribution of fluids provided to, or removed from, tissue site 116.

The flow channels described herein may be created by voids and/or cells in the manifold 122 that are fluidly connected to, or in communication with, adjacent voids and/or cells. The flow channels may be uniform in shape and size, or may include patterned or random variations in shape and size. Variations in shape and size of the voids and/or cells of the manifold 122 may be selectively chosen and used to alter the flow characteristics of fluid and/or exudates through the manifold 122.

The flow channels described herein allow distribution of reduced pressure and/or transportation of exudates and other fluids to and from a particular tissue site. The flow channels provided may be an inherent characteristic of the manifold 122, provided by a porosity of the manifold 122, for example, or the flow channels may be chemically, mechanically, or otherwise formed in the material prior to or after assembly of the manifold 122. In some embodiments, the void, pore, or cell sizes of the manifold 122 described herein may be in the range of about 50 microns to about 600 microns. In other illustrative embodiments, the pore size of the manifold 122 may be from about 400 microns to about 600 microns.

Manifold 122 may be a biocompatible material adapted to be placed in contact with tissue site 116 and distribute reduced pressure across tissue site 116. Examples of manifold 122 may include, without limitation, devices that have structural elements arranged to form flow channels, such as, for example, cellular foam, open-cell foam, porous tissue collections, liquids, gels, and foams that include, or cure to include, flow channels. Manifold 122 may be porous and may be made from foam, gauze, felted mat, or other material suited to a particular biological application. In one embodiment, manifold 122 may be a porous foam and may include a plurality of interconnected cells or pores that act as flow channels. The porous foam may be a polyurethane, open-cell, reticulated foam such as GranuFoam® material manufactured by Kinetic Concepts, Incorporated of San Antonio, Tex. In some embodiments, manifold 122 may also be used to distribute fluids such as medications, antibacterials, growth factors, and other solutions to tissue site 116. Other layers may be included in or on manifold 122, such as absorptive materials, wicking materials, hydrophobic materials, and hydrophilic materials.

In one illustrative embodiment, manifold 122 may be constructed from bioresorbable materials that do not have to be removed from tissue site 116 following use of the system 100. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. Manifold 122 may further serve as a scaffold for new cell-growth, or a scaffold material may be used in conjunction with manifold 122 to promote cell-growth. A scaffold may be a substance or structure used to enhance or promote the growth of cells or formation of tissue, such as a three-dimensional porous structure that may provide a template for cell growth. Illustrative examples of scaffold materials include calcium phosphate, collagen, PLA/PGA, coral hydroxy apatites, carbonates, or processed allograft materials. Scaffold materials may have pore sizes that are large enough to permit ingrowth of tissue into the scaffold. In some embodiments, the pore sizes may be in an upper end of the range of pore sizes of the manifold materials described above.

Drape 124 at least partially covers manifold 122 if positioned over tissue site 116, and a drape aperture 125 extends through drape 124. Drape 124 may provide a fluid seal adequate to maintain reduced pressure at a desired site given a particular reduced-pressure source or subsystem involved. Drape 124 may be, for example, an impermeable or semi-permeable, elastomeric material. An elastomeric material generally refers to a polymeric material that may have rubber-like properties. More specifically, most elastomers may have ultimate elongations greater than 100% and a significant amount of resilience. The resilience of a material refers to the material's ability to recover from an elastic deformation. Elastomers that are relatively less resilient may also be used as these elastomers are more likely to tear if faced with a cutting element. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of materials of drape 124 may include a silicone drape, 3M Tegaderm® drape, and a polyurethane (PU) drape such as one available from Avery Dennison Corporation of Pasadena, Calif. An additional, specific non-limiting example of a material of drape 124 may include a 30 μm matte polyurethane film such as the Inspire™ 2317 manufactured by Exopack™ Advanced Coatings of Matthews, N.C.

A drape adhesive 123 may be positioned between drape 124 and a portion of epidermis 118 surrounding tissue site 116 that may be intact. Drape adhesive 123 may hold drape 124 in place and fluidly seal drape 124 to epidermis 118 surrounding tissue site 116. Fluidly sealing drape 124 to epidermis 118 may refer to sealing of drape 124 to epidermis 118 so that fluid may be inhibited from passing between drape 124 and epidermis 118. Drape adhesive 123 may include another layer such as, for example, a gasket or additional sealing member. Drape adhesive 123 may take numerous forms. For example, in some embodiments, drape adhesive 123 may be a medically acceptable adhesive, such as a pressure-sensitive adhesive, that extends about a portion of, a periphery of, or about all of drape 124. In other embodiments, drape adhesive 123 may be a double-sided drape tape, a paste, a hydrocolloid, a hydro-gel, a silicone gel, an organogel, or other sealing devices or elements. Drape adhesive 123 may also be a sealing ring or other device. In still another example, drape adhesive 123 may be a releasable adhesive material capable of being removed from tissue site 116 and reapplied to tissue site 116. Before use, drape adhesive 123 may be covered by a release liner (not shown) to protect the drape adhesive 123 before being applied to tissue site 116.

Connector 126 may include a flange 130, a primary connector lumen 132, and a secondary connector lumen 134. Flange 130 may be a base member or other suitable device configured to couple connector 126 to another body, such as manifold 122 or drape 124. In some embodiments, connector 126 may be a disc-like member having a first side and a second side. In one illustrative embodiment, connector 126 may be a T.R.A.C.® Pad or Sensa T.R.A.C.® Pad available from KCI of San Antonio, Tex. Connector 126 may allow the reduced pressure to be delivered to the dressing 106. In other exemplary embodiments, connector 126 may also be a conduit inserted through drape 124.

Connector 126 may be used to fluidly couple first conduit 128 to tissue site 116. In some embodiments, flange 130 may couple connector 126 to manifold 122 as shown. In other embodiments, flange 130 may include a flange adhesive applied to a surface of flange 130 so that flange 130 may couple connector 126 to drape 124. Flange 130 may be disposed between drape 124 and manifold 122 as shown, or in another embodiment, flange 130 may be disposed on drape 124 opposite manifold 122. In some embodiments, primary connector lumen 132 may receive reduced pressure through first conduit 128 and may supply reduced pressure to manifold 122. In some embodiments, secondary connector lumen 134 may be a sensing lumen configured to communicate reduced pressure at manifold 122 to an instrumentation unit to determine the pressure at manifold 122. In some embodiments, the instrumentation unit may be therapy unit 108.

As used herein, the term "coupled" may include direct coupling or indirect coupling via a separate object. The term "coupled" also encompasses two or more components that are continuous with one another by virtue of each of the components being formed from the same piece of material. Also, the term "coupled" may include chemical, such as via a chemical bond, mechanical, thermal, or electrical coupling. Fluid coupling may include coupling that may permit fluid to be in communication between designated parts or locations. Pneumatic coupling may mean, in part, that gas or gas pressure may be in communication between the designated parts or locations.

Dressing 106 may be operable to receive fluids from, or supply fluids to, tissue site 116. Dressing 106 may also be a device that collects liquids whether tissue site 116 may be involved or not. In some embodiments, dressing 106 may be a device for removing liquids from an ostomy bag.

First conduit 128 may include more than one lumen, such as a primary lumen 136, and a secondary lumen 138. First conduit 128 may have different shapes and include more or fewer primary lumens 136 and secondary lumens 138. Primary lumen 136 may deliver reduced pressure, and secondary lumen 138 may function as a sensing lumen, for example. If first conduit 128 is coupled to connector 126, primary lumen 136 may be in fluid communication with primary connector lumen 132, and secondary lumen 138 may be in fluid communication with secondary connector lumen 134. As primary lumen 136 may provide reduced pressure to the tissue site 116, exudates and other fluids may be drawn through primary connector lumen 132 and into primary lumen 136. Hence, secondary lumen 138 may be configured to be fluidly isolated from primary lumen 136 so as not to interfere with the process of sensing the pressure.

Figure 4A:
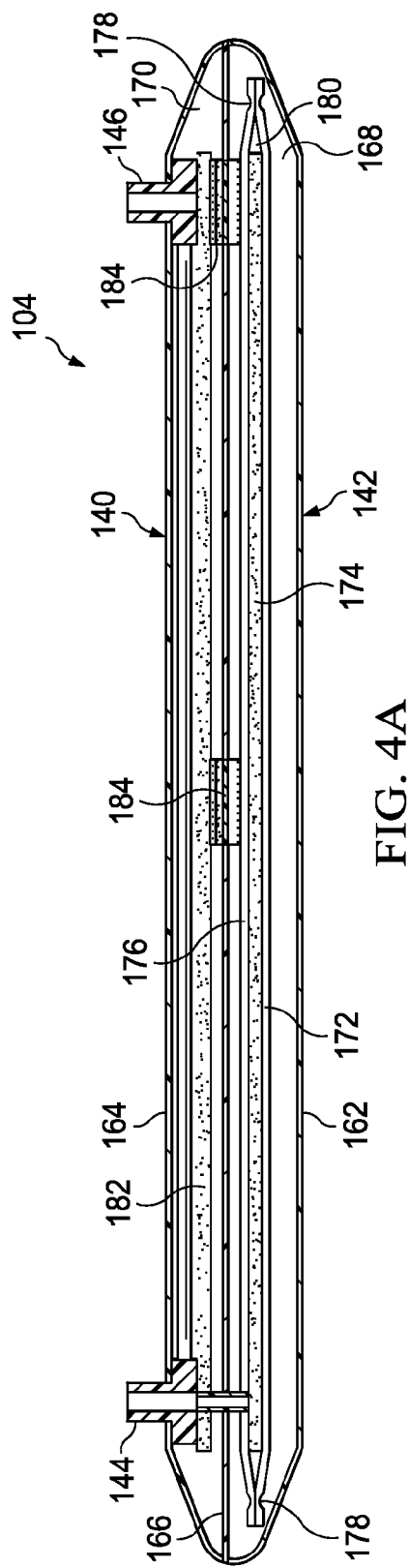
FIG. 4A is a cross-sectional view of the inline storage pouch of FIG. 3A taken along line 4-4.

Pouch 104 may include a side 140 and a side 142 (FIG. 4A). Pouch 104 may also include a port 144, a port 146, and a bypass conduit 148 (shown in hidden lines). In some embodiments, port 144 may be coupled to side 140 of pouch 104. In other embodiments, port 144 may be coupled to side 142 of pouch 104. Similarly, port 146 may be coupled to side 140 of pouch 104, as shown in FIG. 2. In other embodiments, port 146 may be coupled to side 142 of pouch 104. Port 144 and port 146 may be formed on the same side of pouch 104 as shown or may be formed on opposite sides of pouch 104. In some embodiments, port 144 and port 146 may be disposed adjacent to opposite ends of pouch 104. In other embodiments, both port 144 and port 146 may be disposed adjacent the same end. In still further embodiments, port 144 and port 146 may be disposed at other locations of pouch 104. Port 144 may be a device that allows for fluid communication with an interior of pouch 104. Port 144 may provide fluid communication across an outer boundary of pouch 104. In some embodiments, port 144 may include two flow channels that fluidly communicate across a wall of pouch 104. First conduit 128 may be configured to couple to port 144 so that primary lumen 137 and secondary lumen 138 may maintain fluid isolation if coupled to port 144.

In some embodiments, bypass conduit 148 may be a single lumen conduit configured to fluidly couple port 144 and port 146 through the interior of pouch 104. In other embodiments, bypass conduit 148 may include multiple lumens each fluidly coupled to port 144 and port 146. Bypass conduit 148 may be formed in the interior of pouch 104 and may be fluidly isolated from the interior of pouch 104. In some embodiments, bypass conduit 148 may function as a sensing lumen to be fluidly coupled to secondary lumen 138 through port 144. Bypass conduit 148 may also be formed from a portion of pouch 104 that may be fluidly isolated from adjacent portions of pouch 104.

In some embodiments, first conduit 128 may fluidly couple to port 144. Port 144 may be adapted to receive a single lumen or may be adapted to receive multiple lumens as shown. In some embodiments, port 144 may fluidly couple primary lumen 136 of first conduit 128 to the interior of pouch 104. Port 144 may also fluidly couple secondary lumen 138 of first conduit 128 to bypass conduit 148.

Second conduit 150 may include more than one lumen, such as a primary lumen 152 and a secondary lumen 154. Primary lumen 152 may deliver reduced pressure, and secondary lumen 154 may function as a sensing lumen, for example. If second conduit 150 is coupled to port 146, primary lumen 152 may be in fluid communication with the interior of pouch 104, and secondary lumen 154 may be in fluid communication with bypass conduit 148. As primary lumen 152 may provide reduced pressure to pouch 104, exudates and other fluids may be drawn through primary lumen 152. Secondary lumen 154 may be configured to be fluidly isolated from primary lumen 152 so as not to interfere with the process of sensing the pressure.

Port 146 may be a device that allows for fluid communication with the interior of pouch 104. Port 146 may provide fluid communication across an exterior boundary of pouch 104. In some embodiments, port 146 may include two flow channels that fluidly communicate across an exterior boundary of pouch 104. Second conduit 150 may be configured to couple to port 146 so that primary lumen 152 and secondary lumen 154 may maintain fluid isolation from each other if coupled to port 146. Port 146 may receive reduced pressure through primary lumen 152 of second conduit 150, creating a pressure gradient within the interior of pouch 104. The pressure gradient may move fluids from port 144 to port 146. The fluid can be distributed throughout the interior of pouch 104 as the reduced pressure draws from port 146.

Therapy unit 108 may include a reduced-pressure source 156, a pressure sensing unit 158, and one or more pressure sensors 160. Reduced-pressure source 156 may be housed within or used in conjunction with the therapy unit 108. In some embodiments, reduced-pressure source 156 may be an electrically-driven vacuum pump. In other illustrative embodiments, reduced-pressure source 156 may be a manually-actuated or manually-charged pump that does not require electrical power. Reduced-pressure source 156 may be other types of reduced pressure pumps, or may be a wall suction port such as those available in hospitals and other medical facilities. Pressure sensing unit 158 may be in fluid communication with reduced-pressure source 156. Pressure sensing unit 158 may include a microprocessor adapted to process pressure signals, monitor pressure signals, and issue alerts according to a pre-determined pressure therapy for a patient. The pre-determined pressure therapy may include a pressure profile of desired target pressures to be provided to a patient over a time period. The pressure profile may include a set-up profile applying target pressures at the commencement of therapy treatments and a maintenance profile for applying target pressure during therapy. Pressure sensing unit 158 may include sensors, processing units, alarm indicators, memory, databases, software, display units, and user interfaces that further facilitate the application of reduced pressure treatment to the tissue site 116.

In some illustrative embodiments, pressure sensors 160 located in therapy unit 108 may be disposed at or near reduced-pressure source 156. In other illustrative embodiments, pressure sensors 160 may be one or more transducers located in connector 126. Pressure sensors 160 may include an electrical interface (not shown) that can provide the pressure signal measured at or near reduced-pressure source 156. The pressure signal may provide an indication of the pressure between the connector 126 and the manifold 122. The pressure sensors 160 may communicate with pressure sensing unit 158 to monitor and control reduced-pressure source 156. In some illustrative embodiments, pressure sensors 160 may communicate with pressure sensing unit 158 to monitor whether the pressure signal is following the pressure set-up profile. The pressure set-up profile may include an expected increase in the reduced pressure during a predetermined time period detected at the tissue site 116 following initial application of reduced pressure. If the pressure signal does not follow the pressure set-up profile, pressure sensing unit 158 may provide an indication that the pressure signal did not follow the pressure set-up profile. In some embodiments, the indication may be in the form of a visual or audible alert or alarm, for example. If the pressure signal is following the pressure set-up profile, pressure sensing unit 158 may provide an indication that the pressure signal followed the pressure set-up profile. The indication that the pressure set-up profile has been followed may be different than the indication that the pressure set-up profile has not been followed.

Figure 3A:
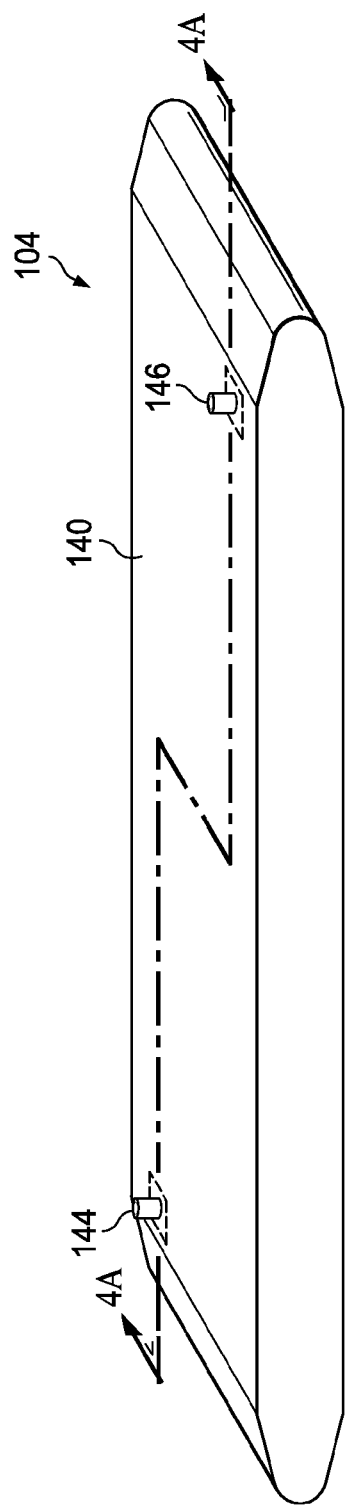
FIGS. 3A and 3B are perspective views of an inline storage pouch that may be associated with the reduced-pressure system of FIG. 1.
Figure 3B:
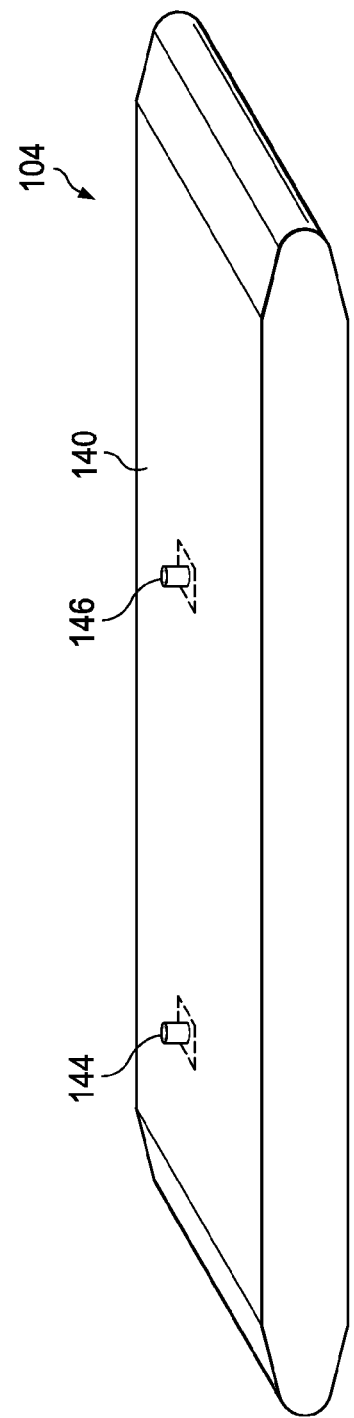
Figure 4B:
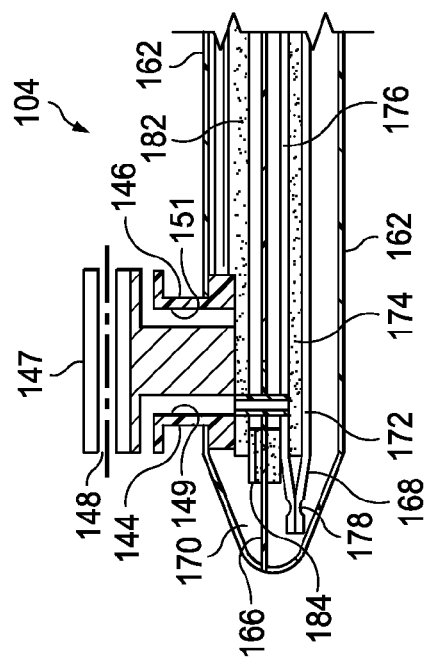
FIG. 4B is a cross-sectional view of a portion of the inline storage pouch of FIG. 4A illustrating an alternative port of the inline storage pouch.

FIGS. 3A and 3B are perspective views, illustrating additional details that may be associated with some embodiments of the pouch 104. FIG. 4A is a cross-sectional view taken along line 4A-4A of FIG. 3A, illustrating additional details that may be associated with some embodiments of the pouch 104, and FIG. 4B is a detail view, illustrating additional details of an alternative portion of the pouch 104 that may be associated with some embodiments. Pouch 104 may be formed with an outer wall 164, an outer wall 162, and a partition wall 166. Outer wall 162 and outer wall 164 may be coupled, such as by welding or the like, on peripheral portions of outer wall 162 and outer wall 164 to form pouch 104 having an interior. As shown in the cross sectional view of FIG. 4A, partition wall 166 may extend from peripheral portions of outer wall 162 and outer wall 164 through the interior to separate the interior into a chamber 168 and a chamber 170. Outer wall 162, outer wall 164, and partition wall 166 may be formed from a liquid impermeable material to prevent liquids within the chamber 168 and the chamber 170 from exiting pouch 104 or communicating through partition wall 166 except as described herein. In some embodiments, the liquid-impermeable material may be formed from the same material used to form the drape 124. In addition, outer wall 164, outer wall 162, and partition wall 166 may be formed from a gas-impermeable material to prevent gas within the chamber 168 and the chamber 170 from exiting pouch 104 or communicating through partition wall 166 except as described herein. Chamber 168 and chamber 170 may generally be fluidly isolated from each other by partition wall 166 except as described in more detail below.

In some embodiments, side 140 may be formed by outer wall 164 so that chamber 170 may be proximate to side 140. Similarly, side 142 may be formed by outer wall 162 so that chamber 168 may be proximate to side 142. As shown in FIG. 3A, port 144 and port 146 may be disposed on side 140. As shown in FIG. 4A, port 144 may be in fluid communication with chamber 168, and port 146 may be in fluid communication with chamber 170. Port 144 and port 146 may also both be located on side 142, or port 144 and port 146 may be disposed on opposite sides of pouch 104. In other embodiments, port 144 and port 146 may be located on pouch 104 in non-peripheral portions of pouch 104, for example, as shown in FIG. 3B.

In some embodiments, chamber 168 may form a fluid storage volume configured to receive and store fluid, for example, from tissue site 116. Chamber 168 may be larger than chamber 170. In some embodiments, a manifold 172 may be disposed within chamber 168. In some embodiments, manifold 172 may be positioned adjacent to outer wall 162 and may span chamber 168. In some embodiments, manifold 172 may be separated from outer wall 162. In other embodiments, manifold 172 may be coupled to outer wall 162 so that manifold 172 may remain in position if pouch 104 is moved, folded, or otherwise disturbed from the orientation illustrated in FIG. 4A. Manifold 172 may be configured to allow passage of, or to channel, fluid through manifold 172. Manifold 172 may provide a flow passage across the interior of chamber 168. In some illustrative embodiments, manifold 172 may be formed from Libeltex TDL2 having a material weight of 80 grams per square member (gsm). In other embodiments, manifold 172 may have a material weight between about 20 gsm and about 140 gsm. Larger material weights may be selected to increase the manifolding properties and the fluid capacity of the manifold 172. Other materials may be used to form manifold 172, such as, woven and non-woven materials, fibrous materials, non-woven Freudenberg M1545N or M1550, non-woven Texsus Multitex, and other similar materials.

An absorbent 174 may be disposed within chamber 168. Absorbent 174 may be disposed proximate to a surface of manifold 172 opposite outer wall 162 so that absorbent 174 may be partially enclosed by manifold 172. In some embodiments, absorbent 174 may be dimensioned to be coextensive with manifold 172. In other embodiments, absorbent 174 may be dimensioned to be slightly smaller than manifold 172 so that manifold 172 may extend past absorbent 174. Absorbent 174 may be coupled to manifold 172 so that absorbent 174 may remain in position in the event that pouch 104 is moved, folded, or otherwise disturbed from the orientation illustrated in FIG. 4A. Absorbent 174 may be coupled by welding, bonding, or securing with an adhesive, for example. In an illustrative embodiment, absorbent 174 may be BASF Luquafleece 402C. Other materials may be used to form absorbent 174, for example, super absorbent polymers disposed on woven and non-woven substrates, fibrous materials, non-woven TAL superabsorbent fiber, non-woven Texsus Absortex, and the like. Absorbent 174 may be configured to absorb liquid, for example, from tissue site 116.

In some embodiments, a manifold 176 may be disposed within chamber 168. In some embodiments, manifold 176 may be positioned adjacent to partition wall 166 and may span chamber 168 between partition wall 166 and absorbent 174. In some embodiments, manifold 176 may be separated from partition wall 166. In some embodiments, manifold 176 may be coupled to partition wall 166 so that manifold 176 may remain in position in the event that pouch 104 is moved, folded, or otherwise disturbed from the orientation illustrated in FIG. 4A. Similarly, manifold 176 may be coupled to absorbent 174, for example, by bonding, welding, or securing with an adhesive.

Manifold 176 may be configured to channel fluid through or allow passage of fluid through manifold 176. Manifold 176 may provide a flow passage within chamber 168 adjacent to partition wall 166. In some illustrative embodiments, manifold 176 may be formed from Libeltex TDL2 having a material weight of 80 gsm. In other embodiments, manifold 176 may have a material weight between about 20 gsm and about 140 gsm. Larger material weights may be selected to increase the manifolding properties and the fluid capacity potential of the manifold 176. Other materials may be used to form manifold 176, for example, woven and non-woven materials, fibrous materials, non woven Freudenberg M1545N or M1550, non-woven Texsus Multitex, and other similar materials.

In some illustrative embodiments, manifold 172 may be coupled to manifold 176 at peripheral portions 178 of manifold 172 and manifold 176. Coupling of manifold 172 and manifold 176 may enclose absorbent 174 within a cavity 180 formed by manifold 172 and manifold 176. Enclosing absorbent 174 within manifold 172 and manifold 176 can provide flow channels or fluid passages around absorbent 174 so that fluid entering chamber 168 may flow freely if not absorbed by absorbent 174. Fluid within chamber 168 may flow through manifold 172 and manifold 176 to interact with, be absorbed by, and be stored within absorbent 174. In addition, reduced pressure supplied to chamber 168 may flow through manifold 172 and manifold 176 unhindered by absorbent 174. In some embodiments, manifold 172, manifold 176, and absorbent 174 may substantially fill chamber 168. In other embodiments, chamber 168 may include only one of manifold 172 and manifold 176.

In some embodiments, chamber 170 may include a manifold 182 disposed therein. Chamber 170 may be smaller than chamber 168. In some embodiments, manifold 182 may be positioned adjacent to outer wall 164 and may span chamber 170. In some embodiments, manifold 182 may be separated from outer wall 164. In some embodiments, manifold 182 may be coupled to outer wall 164 so that manifold 182 may remain in position in the event that pouch 104 is moved, folded, or otherwise disturbed from the orientation illustrated in FIG. 4A. In other embodiments, manifold 182 may be coupled to both outer wall 164 and partition wall 166. Manifold 182 may be configured to allow passage of or to channel fluid through manifold 182. Manifold 182 may provide a flow passage through chamber 170. In some illustrative embodiments, manifold 182 may be formed from Libeltex TDL2 having a material weight of 80 gsm, although other, similar, materials may be used to form manifold 182. For example, woven and non-woven materials, fibrous materials, non-woven Freudenberg M1545N or M1550, non-woven Texsus Multitex, and other similar materials may be suitable for some embodiments of manifold 182. In other embodiments, manifold 182 may have a material weight between about 20 gsm and about 140 gsm. Larger material weights may be selected to increase the manifolding properties and the fluid capacity of the manifold 182.

Pouch 104 may include one or more air bridges, such as filter assemblies 184. In some embodiments air bridges may be fluid passageways through the partition wall 166 that provide for fluid communication between the chamber 168 and the chamber 170. An air bridge may include a liquid barrier, as described below with respect to filter assemblies 184. Two filter assemblies 184 are shown in FIG. 4A, although more or fewer filter assemblies 184 may be used. In some embodiments, a filter assembly 184 may be disposed at each end of pouch 104 proximate to port 144 and port 146, respectively. A filter assembly 184 may be positioned between opposite ends of the pouch 104, for example, near a middle portion of pouch 104. Each filter assembly 184 may be coupled to partition wall 166 and configured to provide a fluid passage across partition wall 166 as described in more detail below.

Figure 5A:
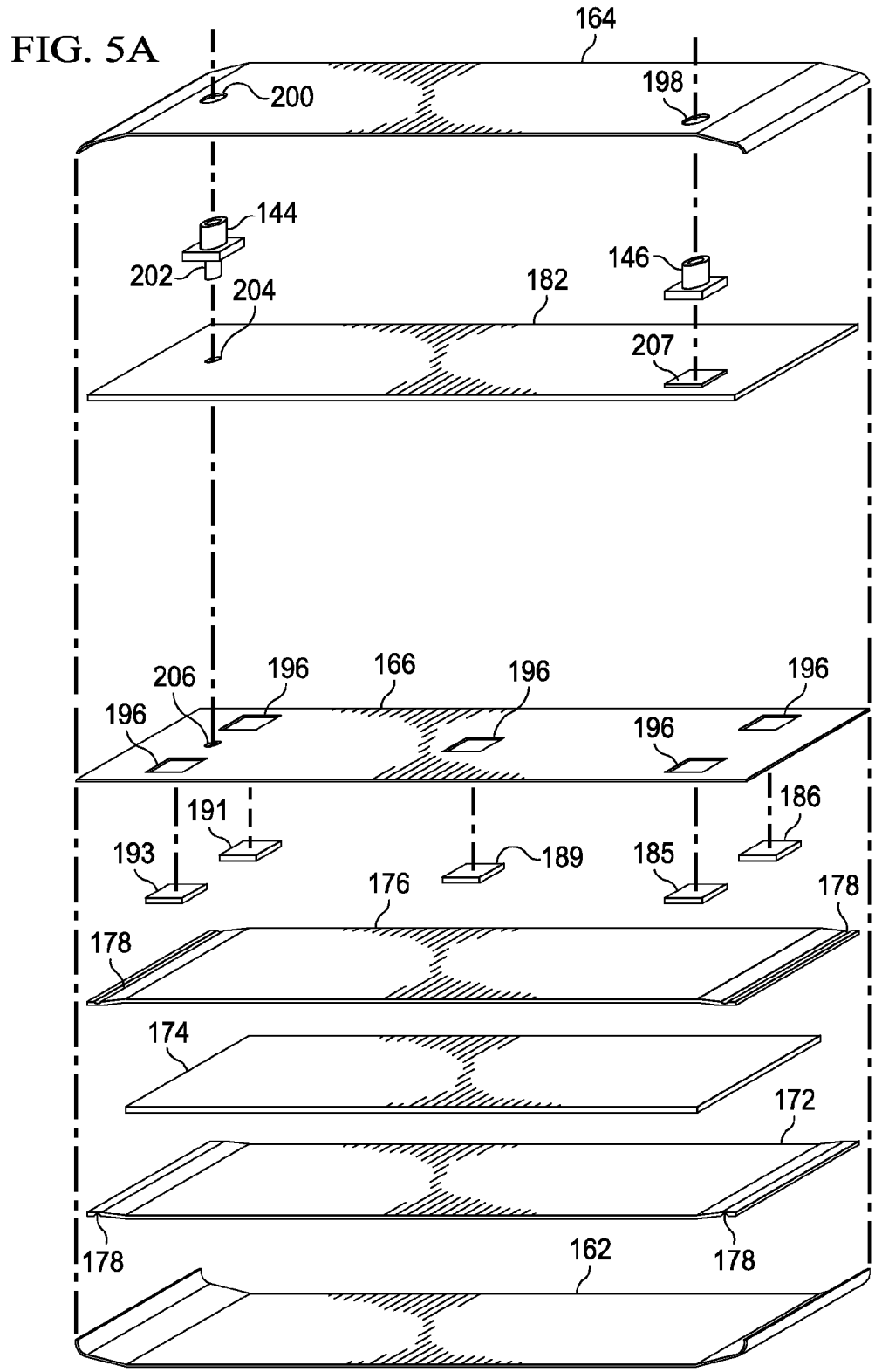
FIGS. 5A and 5B are exploded perspective views of the inline storage pouch of FIG. 3A.
Figure 5B:
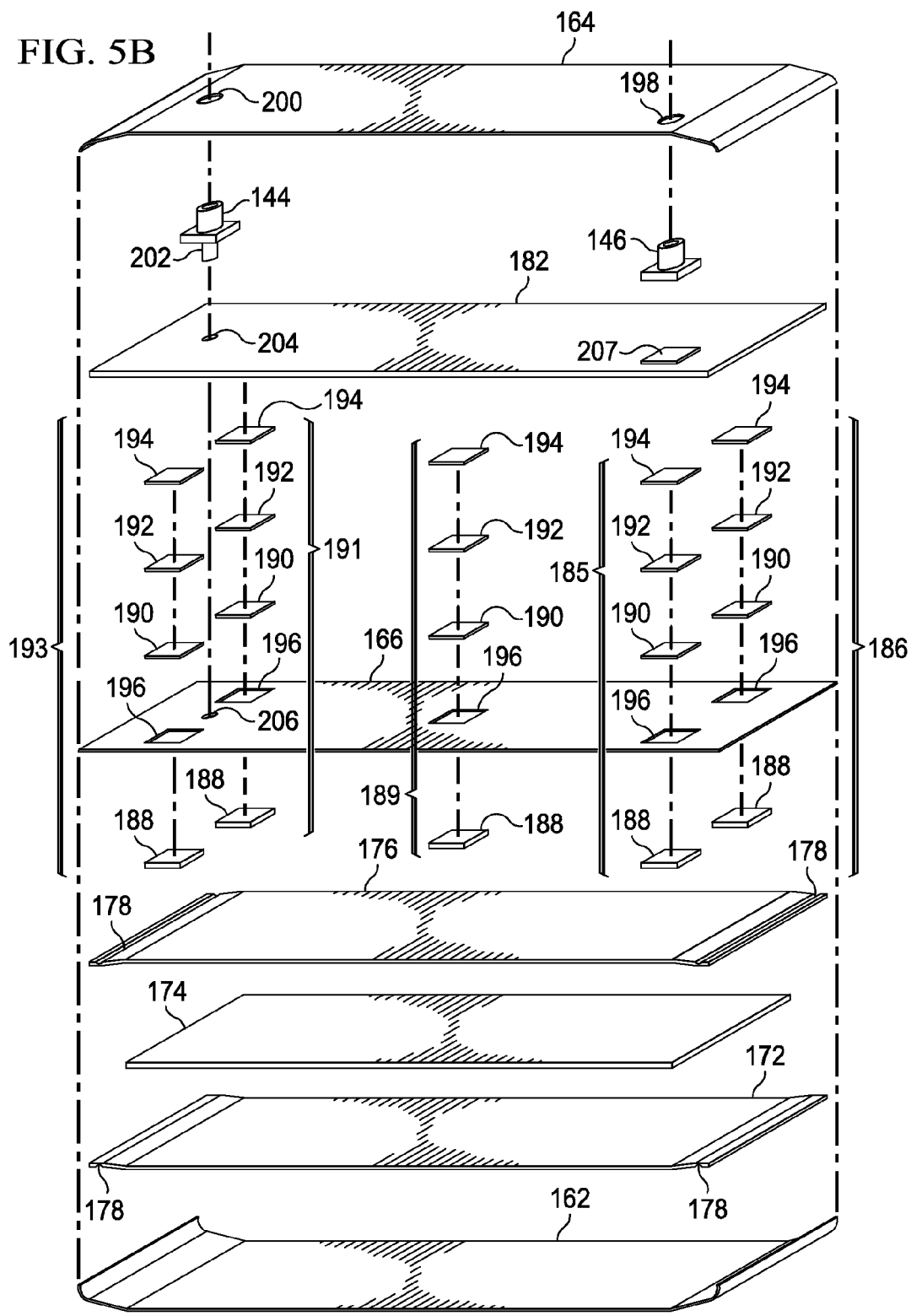
Figure 6:
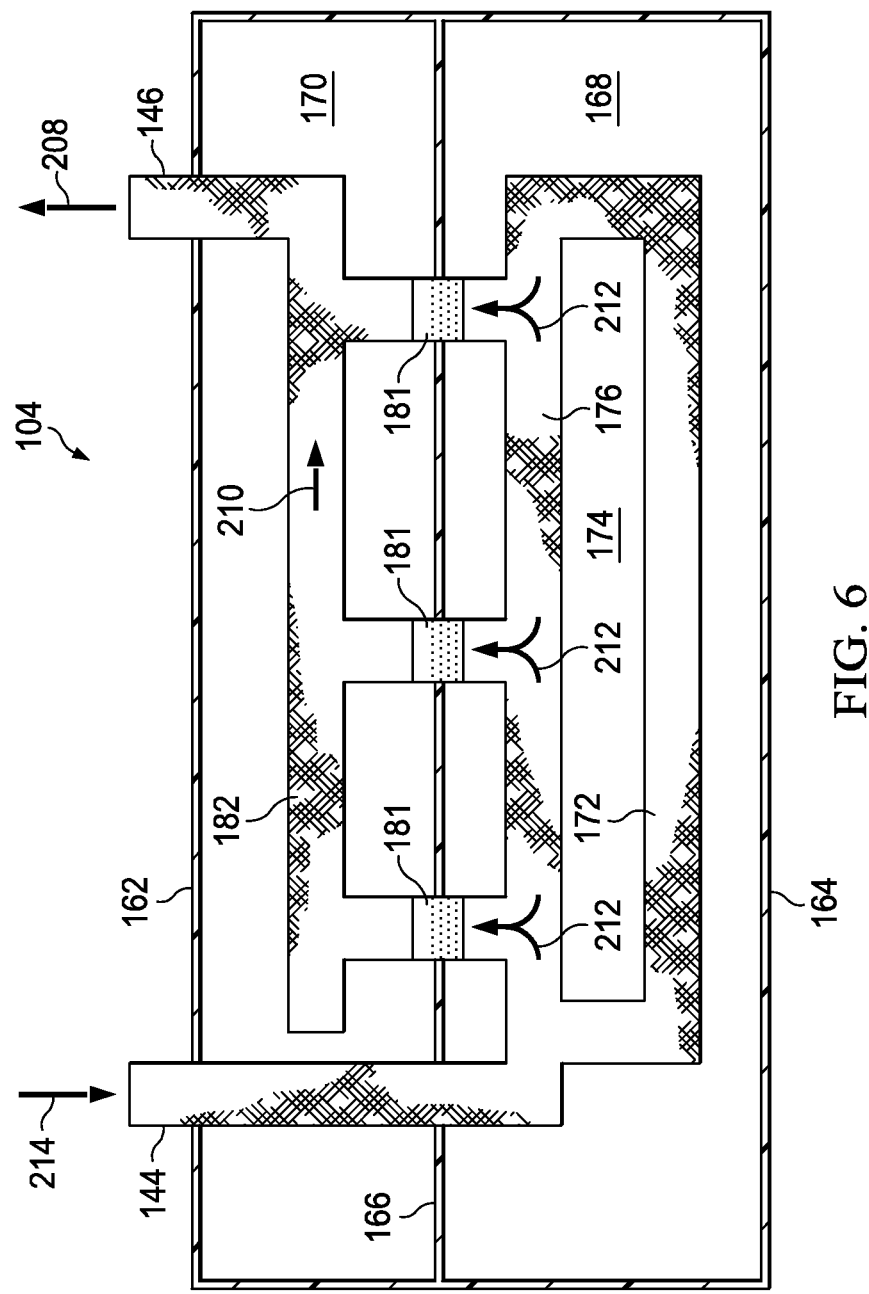
FIG. 6 is a schematic diagram of the inline storage pouch of FIG. 3A.

FIG. 5A and FIG. 5B are exploded views, illustrating additional details that may be associated with some embodiments of the pouch 104. FIG. 6 is a schematic diagram, illustrating additional details that may be associated with some embodiments of the pouch 104. Referring to FIG. 5A, pouch 104 may include five filter assemblies 184. A first filter assembly 185 may be positioned in a corner of pouch 104 proximate to port 146. A second filter assembly 186 may be positioned on a same end but in an adjacent corner of pouch 104. A third filter assembly 189 may be positioned near a middle portion of pouch 104. In some embodiments, third filter assembly 189 may be equidistantly spaced from each end of pouch 104 and each lateral edge of pouch 104. In other embodiments, third filter assembly 189 may be positioned in other locations. A fourth filter assembly 191 may be positioned in a corner of pouch 104 proximate to port 144. A fifth filter assembly 193 may be opposite fourth filter assembly 191. As shown in FIG. 5A, each filter assembly 185, 186, 189, 191, and 193 may be a single filter disposed in the partition wall 166. The filters may be hydrophobic filters so that fluid communication may be limited to communication of reduced pressure, preventing liquid from flowing across partition wall 166. Generally, filters may inhibit liquids from crossing partition wall 166 between chamber 168 and chamber 170. Each filter assembly 185, 186, 189, 191, and 193 may be positioned adjacent to an aperture 196 in partition wall 166. Aperture 196 may permit fluid communication across partition wall 166.

As shown in FIG. 5B, each filter assembly 185, 186, 189, 191, and 193 can also include a first filter 188, a filter manifold 190, a second filter 192, and a filter cap 194. First filter 188 may be positioned between manifold 176 and partition wall 166, proximate to aperture 196 in partition wall 166. First filter 188 and second filter 192 may cover aperture 196 so that fluid passing between chamber 168 and chamber 170 through aperture 196 may flow through first filter 188 and second filter 192. First filter 188 and second filter 192 may be primary filters and may be hydrophobic filters so that fluid communication may be limited to communication of reduced pressure, preventing liquid from flowing across partition wall 166. Generally, first filter 188 and second filter 192 may inhibit liquids from crossing partition wall 166 between chamber 168 and chamber 170. In some embodiments, filter manifold 190 may be a manifold having a size and shape to substantially fill aperture 196. Filter manifold 190 may be formed of a material similar to the material of manifold 172, manifold 176, or manifold 182. Filter manifold 190 may be used to separate first filter 188 and second filter 192 and provide flow channels across partition wall 166. Some embodiments may not include the filter manifold 190. Filter cap 194 may be a polyurethane cap having an aperture to allow fluid communication across filter cap 194. Filter cap 194 may be used to secure second filter 192 and filter manifold 190 to partition wall 166. A charcoal filter or other odor filter may be included in filter assembly 184.

As shown in FIGS. 5A and 5B, outer wall 164 may include an aperture 198 configured to allow a connector of port 146 to extend through outer wall 164 for coupling to second conduit 150 (FIG. 2). Aperture 198 may be sized to be substantially similar to the dimensions of the connector of port 146 and may seal to the connector of port 146 to prevent leaks from pouch 104 around port 146. Aperture 198 may include more than one apertures, for example, may include at least two apertures to accommodate a connector for primary lumen 152 of second conduit 150 and a connector for secondary lumen 154 of second conduit 150. By coupling second conduit 150 to port 146, reduced pressure supplied by reduced pressure source 156 (FIG. 2) may be supplied to chamber 170. Port 146 may be in direct fluid communication with chamber 170 so that primary lumen 152 of second conduit 150 terminates in chamber 170 to supply reduced pressure thereto. A secondary filter 207 may be positioned adjacent to port 146 and between outer wall 164 and manifold 182 so that fluid flowing from chamber 170 into port 146 passes through secondary filter 207. Secondary filter 207 may also include a charcoal filter.

Similarly, outer wall 164 may include an aperture 200 configured to allow a connector of port 144 to extend through outer wall 164 for coupling with first conduit 128 (FIG. 2). Aperture 200 may be sized to be substantially similar to the dimensions of the connector of port 144 and may seal to the connector of port 144 to prevent leaks from pouch 104 around port 144. Aperture 200 may include more than one aperture, for example, aperture 200 may include at least two apertures to accommodate a connector for primary lumen 136 of first conduit 128 and a connector for secondary lumen 138 of first conduit 128. In embodiments where port 144 is positioned on side 140 of pouch 104 adjacent to chamber 170, port 144 may include a penetrating lumen 202 having a length such that penetrating lumen 202 may extend into chamber 168. Manifold 182 may include an aperture 204, and partition wall 166 may include an aperture 206 configured to accommodate and seal to penetrating lumen 202. In some embodiments, penetrating lumen 202 may be fluidly isolated from chamber 170. Penetrating lumen 202 may be configured to allow fluid communication between first conduit 128 and chamber 168 through port 144. First conduit 128 may be coupled to port 144, which may also be fluidly coupled to primary lumen 136 to chamber 168 and penetrating lumen 202. Bypass conduit 148 (FIG. 2), may couple to port 144 and port 146 while passing through chamber 170 to fluidly couple secondary lumen 138 of first conduit 128 to secondary lumen 154 of second conduit 150.

As shown in FIG. 4B, in an alternative embodiment, port 144 and port 146 may be a combined port 147 having a lumen 149 for fluidly connecting chamber 168 to tissue site 116. Combined port 147 may also include a lumen 151 for fluidly connecting chamber 170 to therapy unit 108. Combined port 147 may also include bypass conduit 148. Both lumen 149 and lumen 151 may provide fluid communication into pouch 104. Bypass conduit 148 may be disposed on a portion of combined port 147 exterior to pouch 104, allowing pressure sensing functions of therapy unit 108 to bypass pouch 104. Combined port 147 reduces the number of penetrations into pouch 104 reducing the risk of leak formation.

FIG. 6 is a schematic diagram of pouch 104 illustrating, among other things, fluid flow through pouch 104. As shown schematically in FIG. 6, pouch 104 may include chamber 168 and chamber 170 separated by partition wall 166, which may be common to chamber 168 and chamber 170. Manifold 172 and manifold 176 may be disposed within chamber 168, and manifold 182 may be disposed within chamber 170. Absorbent 174 may be disposed between manifold 172 and manifold 176 in chamber 168. In some embodiments, chamber 168 may not include manifold 172, and absorbent 174 may be disposed proximate to manifold 176. Air bridges 181 may fluidly couple manifold 176 and manifold 182 at extremities of manifold 176 and manifold 182. In some embodiments, air bridges 181 may be gas permeable liquid barriers. Port 144 may fluidly couple to manifold 176, and in some embodiments, port 144 may fluidly couple to manifold 176 and manifold 172 in chamber 168. Port 144 may couple manifold 176 and manifold 172 to a dressing, such as dressing 106 of FIG. 2. Port 146 may fluidly couple manifold 182 in chamber 170 to a reduced-pressure source, such as reduced-pressure source 156 of FIG. 2.

Reduced pressure may be supplied to pouch 104 and manifold 182 through port 146, drawing fluid through port 146 as indicated by flow arrow 208. Reduced pressure may be supplied through manifold 182, drawing fluid through manifold 182 as indicated by flow arrow 210. Reduced pressure may be supplied to manifold 176 and manifold 172 of chamber 168 through air bridges 181, drawing fluid through air bridges 181 as indicated by flow arrows 212. Reduced pressure may be supplied to port 144 through manifold 176 and manifold 172 of chamber 168, drawing fluid through port 144 as indicated by flow arrow 214. As shown, air bridges 181 may provide for fluid communication at more than one location of partition wall 166. Manifold 182 may provide flow channels within chamber 170 to allow the reduced pressure supplied through port 146 to flow to each air bridge 181. Manifold 182 may also prevent collapse of chamber 170 if reduced pressure is supplied to chamber 170. By maintaining a flow channel to each air bridge 181 with manifold 182, manifold 182 may distribute reduced pressure from port 146 to multiple locations of chamber 168.

Figure 7:
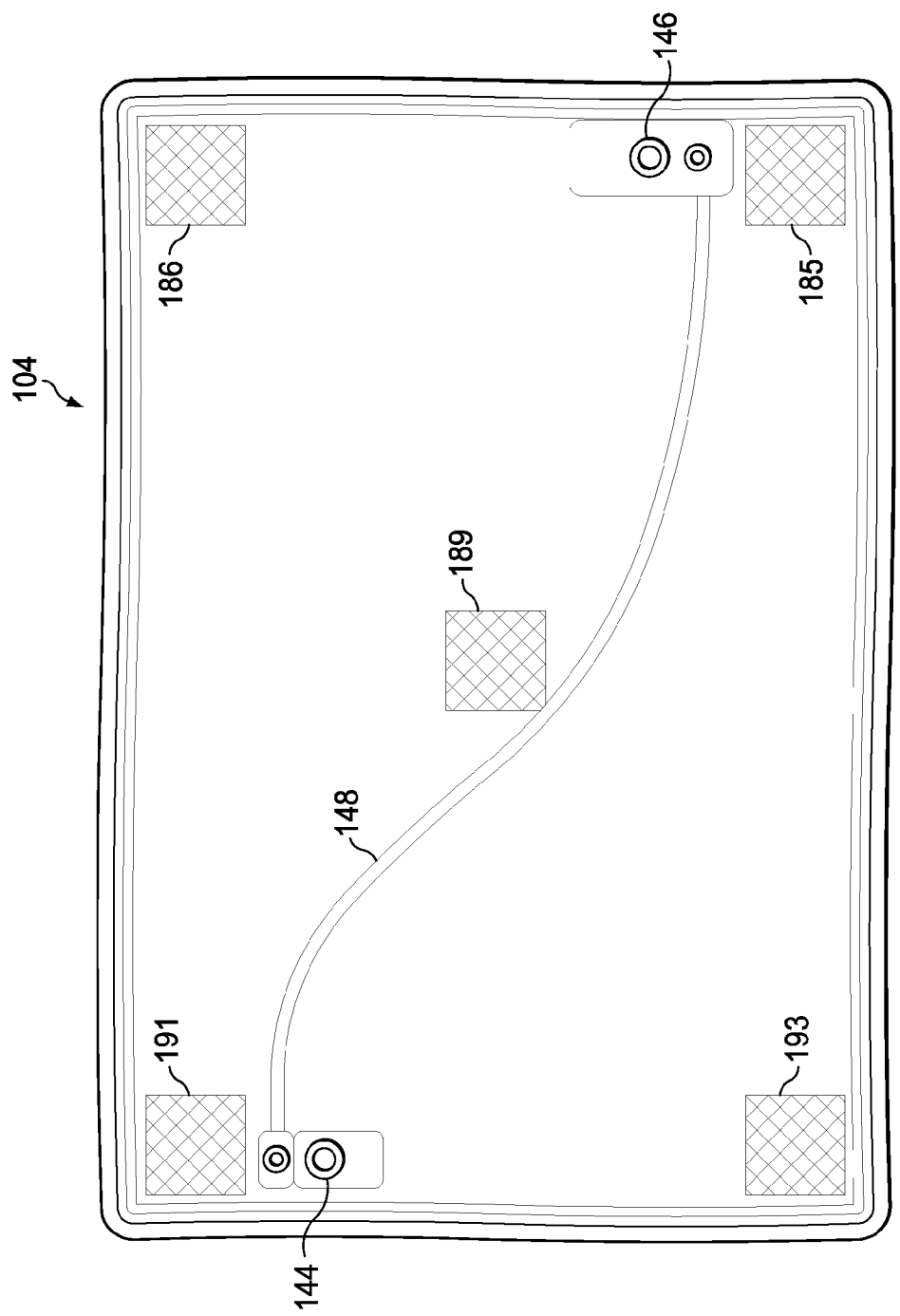
FIG. 7 is an elevation view of the inline storage pouch of FIG. 3A.

Pouch 104 may include more than one filter assembly 184. In the illustrative embodiment of FIGS. 5A, 5B, and 7, five filter assemblies 185, 186, 189, 191, and 193 are shown. In some embodiments, a filter assembly 185, 186 may be placed on opposite corners proximate to port 146. In some embodiments, a filter assembly 189 may be placed proximate to a center portion of pouch 104, and a filter assembly 191, 193 may be placed on opposite corners proximate to port 144. Generally, if reduced pressure is applied to pouch 104 through port 146, the force of the reduced pressure may be strongest proximate port 146, so that fluid flow may be greater through filter assemblies 185, 186 closer to port 146 than through filter assemblies 191, 193 closer to port 144. If chamber 168 is empty, supply of reduced pressure through port 146 may draw liquid from tissue site 116 through port 144 and into chamber 168. As the force of reduced pressure may be strongest proximate to port 146, the liquid may be drawn to and stored in absorbent 174 proximate to filter assemblies 185, 186 closer to port 146. Continued application of reduced pressure may draw more fluid into chamber 168 until the absorbent 174 proximate to port 146 may be saturated, which can cause liquid from tissue site 116 to begin to block flow of reduced pressure through filter assemblies 185, 186 proximate to port 146. Each filter assembly 185, 186, 189, 191, and 193 may prevent passage of liquid across partition wall 166 while permitting the flow of reduced pressure across partition wall 166.

If flow is blocked through filter assemblies 185, 186 proximate to the port 146, reduced pressure may be supplied through port 146 to manifold 182. Manifold 182 may distribute reduced pressure to chamber 168 through filter assemblies 189, 191, and 193 that may be unblocked by liquids in the absorbent 174. Reduced pressure flowing through filter assemblies 189, 191, and 193 may continue to draw liquid through port 144 into chamber 168, continuing to fill chamber 168. As chamber 168 continues to fill, filter assembly 189 may become blocked by liquid. Eventually, continued application of reduced pressure may draw sufficient fluid through port 144 to fill chamber 168, blocking all filter assemblies 185, 186, 189, 191, and 193 with liquid. At this stage, a new pouch 104 may be required for continued application of reduced pressure to tissue site 116.

Figure 8:
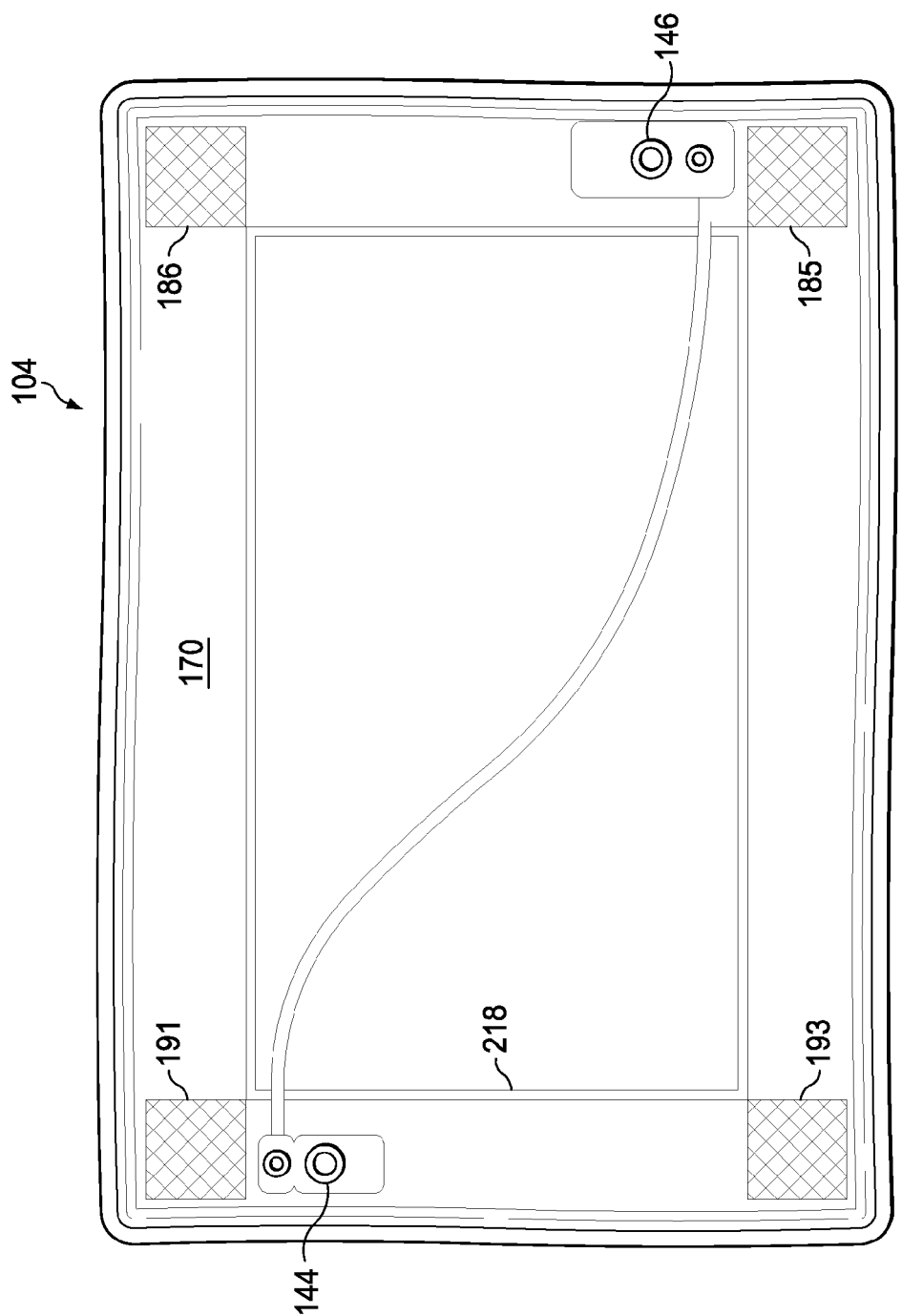
FIG. 8 is an elevation view of another embodiment of an inline storage pouch that may be associated with the reduced-pressure system of FIG. 1.

FIG. 8 illustrates another embodiment of pouch 104 having four filter assemblies 185, 186, 191, and 193 positioned in extremities of the pouch 104. For example, one filter assembly 185, 186, 191, and 193 may be positioned in each corner of pouch 104. FIGS. 9-12 illustrate another embodiment of pouch 104 having three filter assemblies 220, 222, and 224 placed in three extremities of pouch 104. For example, the filter assemblies 220, 222, and 224 may be positioned in three corners of pouch 104. As shown by FIGS. 8-12, pouch 104 may be oriented so that filter assemblies 185, 186, 191, and 193, or filter assemblies 220, 222, and 224 may be supplied with reduced pressure through chamber 170. In some embodiments of FIG. 8, chamber 170 may not extend the entirety of pouch 104. Chamber 170 extends from an outer periphery of the pouch 104 to a channel wall 218 so that fluid may be channeled from port 146 around a perimeter of pouch 104 to each filter assembly 185, 186, 191, and 193. In some embodiments, chamber 170 may be four adjoining cavities extending along a periphery of the pouch 104, bounded by channel wall 218. The adjoining cavities may form four extremities at each corner of pouch 104, for example. In FIGS. 9-12, chamber 170 may have an L-shape formed by two adjoining cavities that extend orthogonally along two sides of pouch 104, bounded by channel wall 218. The two adjoining cavities form three extremities, an extremity at each corner of the L-shape formed by chamber 170, for example. In each embodiment, chamber 170 may provide a flow passage to each filter assembly 220, 222, and 224, but chamber 170 may not be coextensive with chamber 168.

Figure 9:
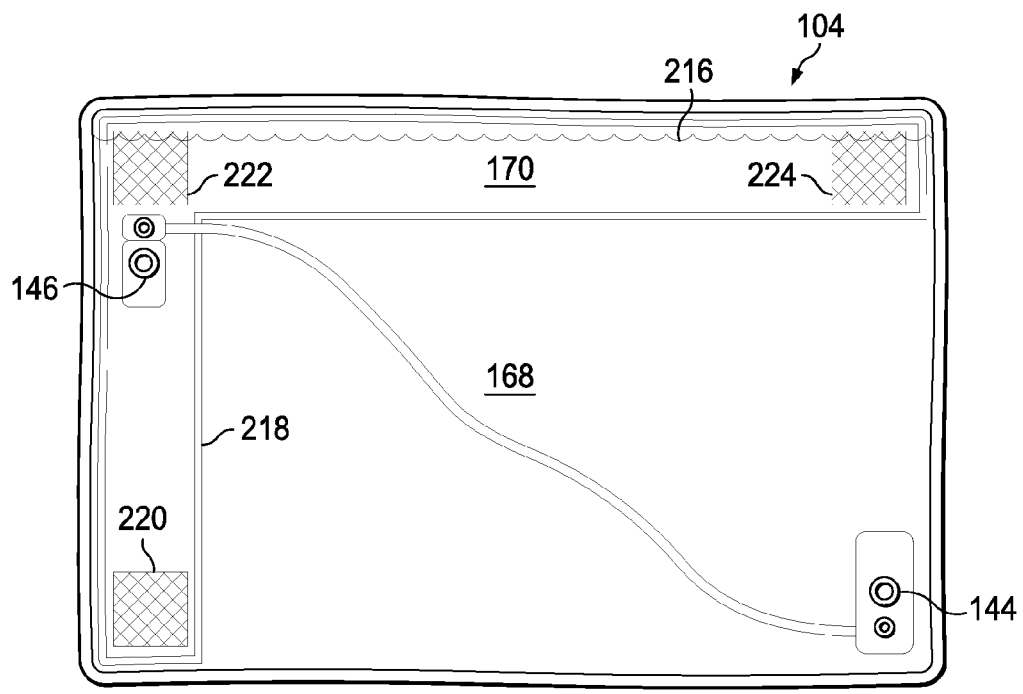
FIG. 9 is an elevation view of another embodiment of an inline storage pouch having fluid stored therein.
Figure 10:
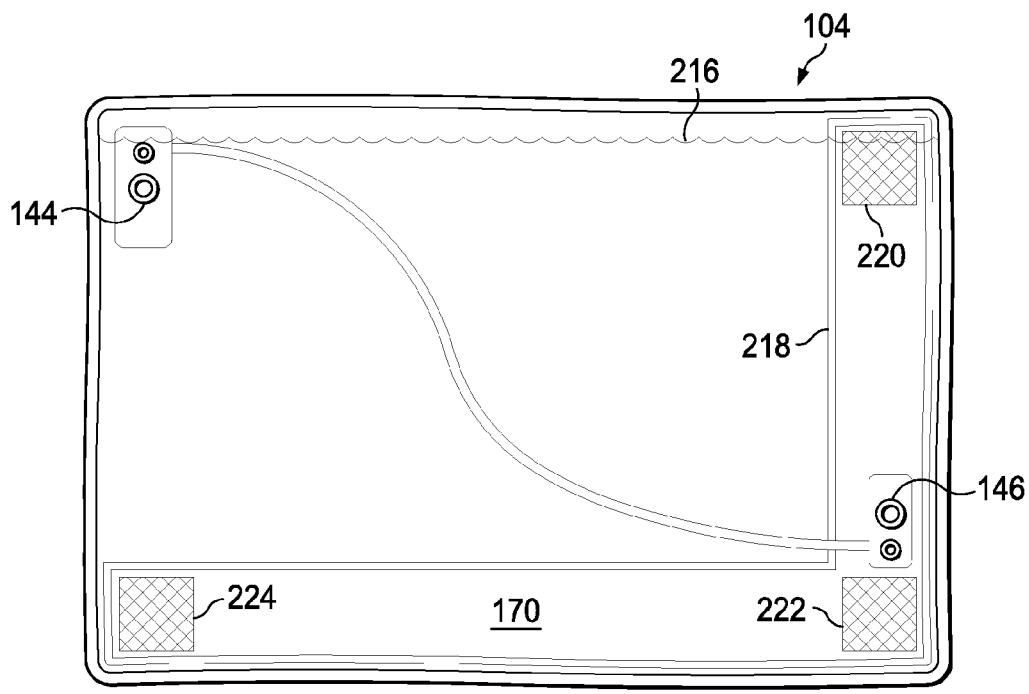
FIG. 10 is an elevation view of the inline storage pouch of FIG. 9 having fluid stored therein, in a second orientation.
Figure 11:
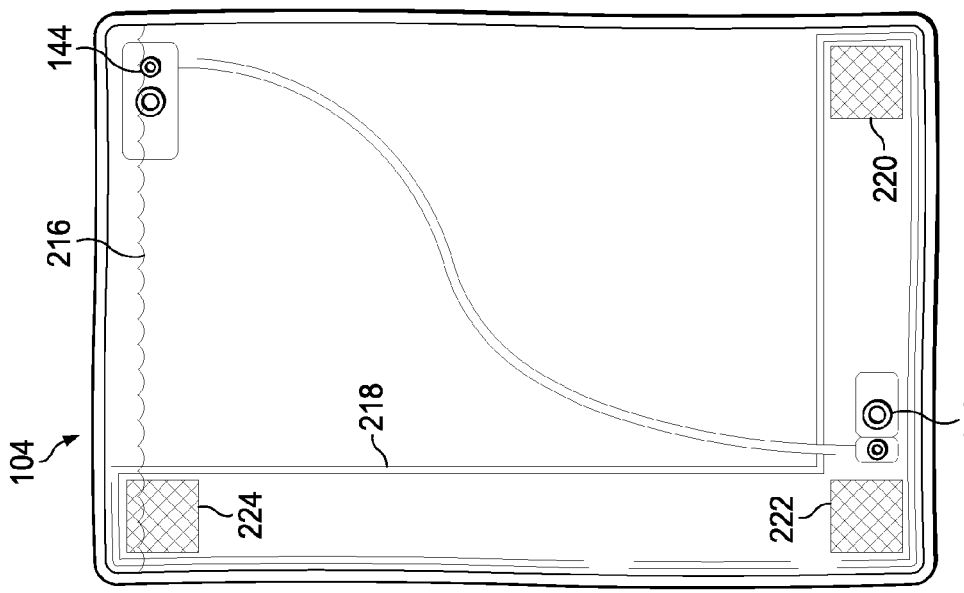
FIG. 11 is an elevation view of the inline storage pouch of FIG. 9 having fluid stored therein, in a third orientation.
Figure 12:
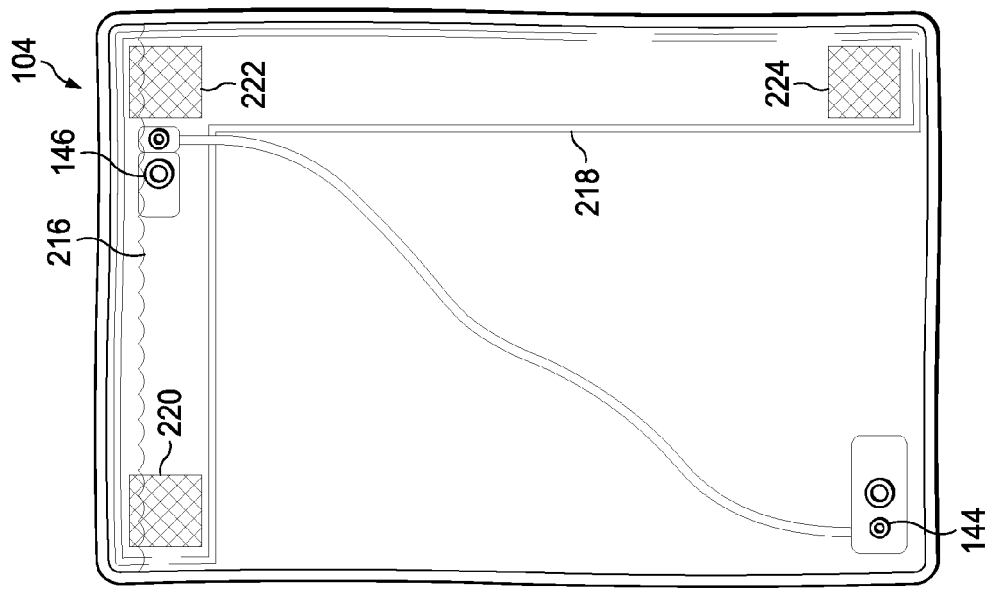
FIG. 12 is an elevation view of the inline storage pouch of FIG. 9 having fluid stored therein, in a fourth orientation.

Chamber 170 and filter assemblies 184 may permit orientation of pouch 104 in a variety of manners without inhibiting the ability of pouch 104 to substantially fill. Referring to FIGS. 9-12, each pouch 104 may include three filter assemblies 220, 222, and 224. In each of FIGS. 9-10, the ground, or a position of lower relative elevation may be oriented parallel to the bottom of the page. As shown in FIG. 9, pouch 104 may be oriented so that a lateral edge is parallel to the ground and port 144 may be proximate to the ground. As pouch 104 fills with liquid, chamber 168 may fill so that filter assembly 220 may be blocked prior to filter assemblies 222 and 224. In the orientation of FIG. 9, reduced pressure may continue to be supplied to chamber 168 until a liquid level 216 reaches filter assemblies 222 and 224, at which point chamber 168 may be substantially filled. As shown in FIG. 10, pouch 104 may be oriented so that a lateral edge is parallel to the ground and port 146 may be proximate to the ground. As pouch 104 fills with liquid, chamber 168 may fill so that filter assembly 222 and filter assembly 224 may be blocked prior to filter assembly 220. In the orientation of FIG. 10, reduced pressure may continue to be supplied to chamber 168 until liquid level 216 reaches filter assembly 220, at which point chamber 168 may be substantially filled. As shown in FIG. 11, pouch 104 may be oriented so that an end is parallel to the ground and second port 146 may be proximate to the ground. As pouch 104 fills with liquid, chamber 168 may fill so that filter assembly 220 and filter assembly 222 may be blocked prior to filter assembly 224. In the orientation of FIG. 11, reduced pressure may continue to be supplied to chamber 168 until liquid level 216 reaches filter assembly 224, at which point chamber 168 may be substantially filled. As shown in FIG. 12, pouch 104 may be oriented so that an end may be parallel to the ground and port 144 is proximate to the ground. As pouch 104 fills with liquid, chamber 168 may fill so that filter assembly 224 may be blocked prior to filter assembly 220 and filter assembly 222. In the orientation of FIG. 12, reduced pressure may continue to be supplied to chamber 168 until liquid level 216 reaches filter assembly 220 and filter assembly 222, at which point chamber 168 may be substantially filled. Pouch 104 may also be oriented so that an edge may be not parallel to the ground. In each orientation, a filter assembly 220, 222, and 224 may be positioned to allow continued supply of reduced pressure to chamber 168 until chamber 168 may be substantially filled.

Although illustrated as a rectangular body herein, pouch 104 may have other suitable shapes, such as circular, triangular, square, or an amorphous shape. Other shaped pouches 104 may also include air bridges 181 disposed at desired locations to allow for substantial filling of the corresponding fluid storage volume, such as chamber 168.

The systems and methods described herein may provide significant advantages, some of which have already been mentioned. For example, pouch 104 may provide a multi-orientation flexible canister. The flexible canister can manifold fluid from multiple points around the canister using air bridges. The air bridges may allow flow of fluid and air even if one or more of the air bridges is blocked, and application of reduced pressure can continue until all air bridges are blocked. In this manner, the flexible canister can fill to its full capacity in multiple orientations. Air bridges located in each corner of the pouch 104 and one positioned centrally may provide for more orientations of the pouch 104, allowing a curved profile, such as a saddle profile of fluid filling.

Although certain illustrative, non-limiting embodiments have been presented, it should be understood that various changes, substitutions, permutations, and alterations can be made without departing from the scope the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, features of any of the embodiments described above may be combined with features of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A system for treating a tissue site with reduced pressure, the system comprising:
    a reduced-pressure source;
    a pouch in fluid communication with the reduced pressure source;
    a dressing in fluid communication with the pouch;
    wherein the pouch comprises:
        a first wall;
        a second wall having a periphery coupled to the first wall to form an interior;
        a third wall extending through the interior to form a first chamber in fluid communication with the dressing and a second chamber in fluid communication with the reduced pressure source; and
        a plurality of filters positioned in the third wall, the filters permitting fluid communication between the first chamber and the second chamber.

2. The system of claim 1, further comprising:
    a first manifold positioned within the first chamber;
    a second manifold coupled to the first manifold to form a cavity; and
    an absorbent disposed in the cavity.

3. The system of claim 1, wherein the pouch comprises at least one corner and one of the filters is positioned in the third wall proximate to the corner.

4. The system of claim 1, wherein the pouch has four corners and the filters are positioned in the third wall proximate to each corner.

5. The system of claim 1, wherein each of the filters is positioned in the third wall proximate to a middle portion of the pouch.

6. The system of claim 1, having at least three filters positioned in the third wall.

7. The system of claim 1, wherein the pouch further comprises:
    a first end and a second end opposite the first end;
    a first port coupled to at least one of the first wall and the second wall, the first port in fluid communication with the first chamber; and
    a second port coupled to at least one of the first wall and the second wall, the second port in fluid communication with the second chamber.

8. The system of claim 1, wherein the pouch further comprises:
    a first end and a second end opposite the first end;
    a first port coupled to at least one of the first wall and the second wall, the first port in fluid communication with the first chamber;
    a second port coupled to at least one of the first wall and the second wall, the second port in fluid communication with the second chamber; and
    wherein the first port is positioned proximate to the first end and the second port is positioned proximate to the second end.

9. The system of claim 1, wherein the pouch further comprises:
a first end and a second end opposite the first end;
a first port coupled to at least one of the first wall and the second wall, the first port in fluid communication with the first chamber to provide fluid communication between the dressing and the first chamber;
a second port coupled to at least one of the first wall and the second wall, the second port in fluid communication with the second chamber to provide fluid communication between the reduced-pressure source and the second chamber;
wherein the first port is positioned proximate to the first end and the second port is positioned proximate to the second end; and
wherein a first filter and a second filter are positioned on the third wall proximate to separate corners of the second end and a third filter is positioned on the third wall proximate to a corner of the first end.

10. The system of claim 7, further comprising a bypass conduit fluidly coupling the first port and the second port through the second chamber.

11. The system of claim 1, wherein the pouch further comprises a port coupled to at least one of the first wall and the second wall, the port having a first lumen in fluid communication with the first chamber to provide fluid communication between the dressing and the first chamber and a second lumen in fluid communication with the second chamber to provide fluid communication between the reduced-pressure source and the second chamber.

12. The system of claim 1, wherein the pouch further comprises a port coupled to at least one of the first wall and the second wall, the port having a first lumen in fluid communication with the first chamber to provide fluid communication between the dressing and the first chamber, a second lumen in fluid communication with the second chamber to provide fluid communication between the reduced-pressure source and the second chamber, and a third lumen disposed exterior of the pouch for providing fluid communication between the dressing and the reduced-pressure source.

13. The system of claim 1, wherein the filters are positioned in the third wall to provide fluid communication between the first chamber and the second chamber if a level of the liquid in the first chamber is less than a level of the liquid in the first chamber if the first chamber is substantially filled.

14. The system of claim 1, further comprising a manifold positioned in the second chamber for providing a flow path within the second chamber.

15. A pouch for storing fluids from a tissue site, the pouch comprising:
a first wall;
a second wall having a peripheral portion coupled to the first wall to form an interior;
a third wall extending through the interior, forming a first chamber adapted to be in fluid communication with a dressing, and forming a second chamber adapted to be in fluid communication with a reduced pressure source; and
a plurality of filters positioned in the third wall, the filters permitting fluid communication between the first chamber and the second chamber;
wherein reduced pressure supplied to the second chamber is supplied to the first chamber through the filters.

16. The pouch of claim 15, further comprising:
a first manifold positioned adjacent the first wall within the first chamber;
a second manifold having flow channels disposed therein and positioned adjacent the third wall, the first manifold and the second manifold coupled together to form a cavity; and
an absorbent disposed in the cavity.

17. The pouch of claim 15, wherein the pouch has one or more corners and a filter of the plurality of filters is positioned on the third wall proximate to each corner.

18. The pouch of claim 15, wherein the pouch has four corners and a filter of the plurality of filters is positioned in the third wall proximate to each corner.

19. The pouch of claim 15, further comprising a filter positioned on the third wall proximate to a center portion of the pouch.

20. The pouch of claim 15, wherein the pouch further comprises:
a first end and a second end opposite the first end;
a first port coupled to at least one of the first wall and the second wall, the first port in fluid communication with the first chamber to provide fluid communication between the dressing and the first chamber;
a second port coupled to at least one of the first wall and the second wall, the second port in fluid communication with the second chamber to provide fluid communication between the reduced-pressure source and the second chamber; and
wherein the first port is positioned proximate to the first end and the second port is positioned proximate to the second end, each end having two corners.

21. The pouch of claim 20, wherein a first filter and a second filter are positioned in the third wall proximate to separate corners of the second end and a third filter is positioned on the third wall proximate to a corner of the first end.

22. The pouch of claim 15, further comprising a bypass conduit fluidly coupling a first port and a second port through the second chamber.

23. The pouch of claim 15, wherein the filters are positioned on the third wall to provide fluid communication between the first chamber and the second chamber if a level of the liquid in the first chamber is less than a level of the liquid in the first chamber if the first chamber is substantially filled.

24. The pouch of claim 15, further comprising a manifold having a plurality of flow channels positioned in the second chamber for providing a flow path within the second chamber.

25. The pouch of claim 15, wherein the plurality of filters are gas permeable and liquid impermeable.

26. A method for treating a tissue site with reduced pressure, the method comprising:
providing a reduced-pressure source;
providing a dressing proximate to the tissue site;
providing a pouch comprising:
a first wall;
a second wall coupled to the first wall on peripheral portions of the first wall and the second wall to form an interior;
a third wall extending through the interior to form a first chamber and a second chamber;
a plurality of filter assemblies positioned in the third wall, the filter assemblies permitting fluid communication between the first chamber and the second chamber, each filter assembly separated from adjacent filter assemblies;

fluidly coupling the reduced-pressure source to the second chamber;

fluidly coupling the dressing to the first chamber;

supplying reduced pressure to the dressing through the second chamber, filter assemblies, and the first chamber; and receiving and storing liquids in the first chamber in response to the supply of reduced pressure.

* * * * *